United States Patent [19]

Roth et al.

[11] 4,329,449

[45] May 11, 1982

[54] METHOD OF USING RECYCLED MOTHER LIQUORS TO PRODUCE ALDOSIDES

[75] Inventors: Claris D. Roth; Kenneth B. Moser; William A. Bomball, all of Decatur, Ill.

[73] Assignee: A. E. Staley Manufacturing Company, Decatur, Ill.

[21] Appl. No.: 126,257

[22] Filed: Mar. 3, 1980

Related U.S. Application Data

[63] Continuation-in-part of Ser. No. 938,750, Sep. 1, 1978, Pat. No. 4,223,129.

[51] Int. Cl.$^3$ .............................................. C07H 1/00
[52] U.S. Cl. .................................... 536/18.6; 536/120
[58] Field of Search ................................... 536/4, 120

[56] References Cited

U.S. PATENT DOCUMENTS

| | | | |
|---|---|---|---|
| 2,606,186 | 8/1952 | Dean et al. | 536/4 |
| 3,346,558 | 10/1967 | Roth | 536/4 |
| 3,375,243 | 3/1968 | Nevin et al. | 536/4 |
| 3,450,690 | 6/1969 | Gibbons et al. | 536/4 |
| 3,565,885 | 2/1971 | Molotsky et al. | 536/4 |
| 3,598,865 | 8/1971 | Lew | 536/4 |
| 3,707,535 | 12/1972 | Lew | 536/4 |
| 3,772,269 | 11/1973 | Lew | 536/4 |
| 3,928,318 | 12/1975 | Panusch et al. | 536/4 |
| 4,223,129 | 9/1980 | Roth | 536/4 |

*Primary Examiner*—Johnnie R. Brown
*Attorney, Agent, or Firm*—M. Paul Hendrickson; Charles J. Meyerson

[57] ABSTRACT

The present invention relates to the preparation of aldoside mixtures, recovering at least a portion of one aldoside component therefrom and reusing the remaining portion of the aldoside mixture to prepare additional aldoside. The aldoside mixture may be prepared by slurrying the carbohydrate in alcohol and passing the slurry through a continuous reactor at an elevated temperature under fluid pressure in the presence of an acid catalyst. The resultant aldoside mixture may then be partitioned into a mother liquor portion and an aldoside portion by selectively recovering at least a portion of one aldoside from the crude aldoside mixture with the remaining mother liquor being recycled.

Crude glycoside mixtures prepared from starch and methanol slurries are suitable substrates for selectively recovering methyl-alpha-D-glucopyranoside. The methyl-alpha-D-glucopyranoside may be easily crystallized and recovered from the glycoside mixture because of its lower solubility in methanol. The resultant mother liquor (rich in the remaining components of the glycoside mixture) in combination with freshly added starch and methanol provides a reaction medium which optimizes methyl-alpha-D-glucopyranoside production.

17 Claims, No Drawings

METHOD OF USING RECYCLED MOTHER LIQUORS TO PRODUCE ALDOSIDES

BACKGROUND

This application is a continuation-in-part of U.S. application Ser. No. 938,750 filed Sept. 1, 1978, now U.S. Pat. No. 4,223,129 entitled "Continuous Process For Making Alkyl Aldosides From Starch or Other Carbohydrates".

Alkyl aldosides have been used as an intermediate products in the manufacture of various chemicals, such as surfactants, glycoside polyols, etc. Because these alkyl aldosides are primarily used to synthesize other chemical products, the aldoside purity becomes a very important factor affecting its ultimate usefulness. Alpha methyl-D-glucoside, an alkyl aldoside, is a particularly useful intermediate, provided it could be inexpensively and expeditiously manufactured in a relatively pure form from inexpensive raw materials.

Alpha methyl glucosides are typically manufactured by the alcoholysis of a monosaccharide (e.g. dextrose) with methanol in a batch process. The reaction product is comprised primarily of four alkyl monosaccharide isomers (methyl-alpha-D-glucopyranoside; methyl-beta-D-glucopyranoside; methyl-alpha-D-glucofuranoside and methyl-beta-D-glucofuranoside). These isomers have different temperatures of crystallization. This facilitates the separation and recovery of methyl-alpha-D-glucopyranoside (frequently referred to as methyl-alpha-D-glucoside) therefrom. This process yields a purer methyl-alpha-D-glucopyranoside product when compared to glucosides prepared from polysaccharides.

The alcoholysis of starch typically produces a crude alkyl glycoside mixture which, in addition to the methyl-alpha-D-glucopyranoside, also contains a variety of other contaminants. The manufacture of methyl-D-glucoside directly from starch has not been practical because of numerous processing and production difficulties (e.g. excessive and undesirable by-product contamination, prolonged and tedious refining steps required to produce a relatively pure product, costly capital equipment investments, incomplete conversion of the raw materials into the desired end-product, low yields, etc.). The use of starch as a starting raw material to continuously manufacture and recover methyl-alpha-D-glucopyranoside from crude glycoside mixtures would be highly desirable.

PRIOR ART

Numerous methods for producing alkyl glucosides have been proposed. U.S. Pat. No. 2,276,621 discloses batch alcoholysis of starch. By concentrating the crude reaction product, methyl-alpha-D-glucoside may be selectively crystallized therefrom. The resultant mother liquor (obtained after crystallization of the alpha methyl glucoside therefrom) is described as a disequilibrate solution of methyl glucoside deficient in methyl alpha glucoside. By adding starch, methanol and catalyst thereto, the mother liquor may be recycled and reused in a batch reaction. It is indicated that this operation may be repeated until the accumulation of by-product is so great as to render further conversion with the original mother liquor impractical.

U.S. Pat. No. 2,606,186 by Dean et al. discloses the use of a column reactor containing a cation exchange resin to catalyze and convert anhydrous dextrose and methanol into methyl glucoside at a reaction temperature less than about 100° C.

In U.S. Pat. No. 3,296,245 crude alkyl glycoside mixtures are reportedly produced by the batch alcoholysis of starch in the presence of a Lewis acid catalyst at an elevated temperature and pressure. The methyl alpha glucoside is recovered from the crude mixture and the mother liquor reportedly may be recycled and reused in the batch reactor several times (2–5 times).

A patent by Molotsky et al. (U.S. Pat. No. 3,565,885) discloses a batch process for preparing an alkali color stable glucoside. Undesirable by-product contamination is reduced by using dextrose as a starting material. An ion-exchange treatment is used to remove reaction product impurities. After recovering the glucoside, the ion-exchanged mother liquor reportedly may be recycled. Carefully controlled conditions (e.g. dextrose starting material, temperature, pH and pressure control, ion exchange, additional refining, etc.) are required to produce a relatively pure product.

Gibbons et al. (U.S. Pat. No. 3,450,690) is similarly concerned with the removal of alkali labile, color producing bodies from crude alkyl glycosides. In Example 1, a crude alkyl glycoside is obtained by passing an anhydrous dextrose and methanol solution through a column packed with a strong cationic resin (e.g. sulfonated crosslinked polystyrene in acid form). The reaction is conducted at a relatively low reaction temperature to protect the resin. A clear alkyl glycoside solution is obtained by refluxing the crude alkyl glycoside reaction product with a base (e.g. 69° C., 30 minutes, pH 12), followed by its cooling and filtration. The alkali treatment reportedly converts the undesirable contaminants (non-glucosides) into a form which can be readily separated and removed (e.g. filtration, chemical treatment, ion exchange treatment, etc.) without causing the alkyl glucosides to crystallize therefrom.

More recently, U.S. Pat. No. 3,375,243 (Nevin et al.) discloses a method of making methyl glucosides from starch using p-toluene sulfonic acid catalyst in a pressure reactor (e.g. 165° C.–275 psig). Approximately 85–90% of the starch is reported as being converted into methyl glucoside.

Panusch et al. in U.S. Pat. No. 3,928,318 disclose an anhydrous batch process for making methyl glucoside by the alcoholysis of glucose. Crystalline alpha-methyl glucoside is recovered from the reaction mixture and the mother liquor is recycled and reused in the batch reactor.

A continuous method for preparing polyol glucosides is disclosed by Roth et al. (U.S. Pat. No. 3,346,558). In the Roth et al. patent, a non-fluid feed mixture of starch, polyol and acid catalyst is converted to a polyol glycoside by mechanically working and shearing the mixture under elevated temperatures and pressures.

SUMMARY OF THE INVENTION

According to the present invention there is provided a process for directly converting monohydric alcohols and carbohydrates into crude aldosides and recovering therefrom at least one hydrocarbyl aldoside, said process comprising the steps of:

(a) providing to a tubular reaction zone under a positive fluid pressure, a fluid slurry comprised of mother liquor, carbohydrate, monohydric alcohol and catalyst in an amount sufficient to permit chemical conversion of the fluid slurry into a fluid hydrocarbyl aldoside mixture;

(b) heating said feed slurry within said continuous tubular reaction zone to an elevated temperature for a period of time sufficient to convert said fluid slurry into a fluid hydrocarbyl aldoside mixture comprised of hydrocarbyl-alpha aldoside and hydrocarbyl-beta aldoside while continuously providing additional feed slurry to said tubular reaction zone under a positive fluid pressure to force the converted fluid aldoside mixture through said tubular reaction zone;

(c) partitioning the fluid hydrocarbyl aldoside mixture into a mother liquor portion and aldoside portion by selectively recovering at least one hydrocarbyl aldoside from the fluid hydrocarbyl aldoside mixture;

(d) recovering the partitioned aldoside therefrom and recycling the mother liquor to the feed slurry of step (a) above.

Smaller equipment with less necessary capital investment can be effectively used to continuously produce relatively large quantities of a relatively pure aldoside. Because the total reaction cycle takes less time, the process is more energy efficient. There is no separate "heat-up", which saves considerable energy. The total reaction may be completed within 6–15 minutes.

The present method is capable of producing a glycoside mixture of high glucoside purity. The continuous reaction conditions assure that a product of more uniform, acceptable quality will be obtained, since the reagents are thoroughly mixed, and each part of the starch slurry is subjected to substantially the same conditions of temperature and pressure. The key to the success for producing a more pure methyl-alpha-D-glucopyranoside at a higher total yield is in the fact that the alcohol-slurried starch is heated very quickly to obtain the catalyzed alcoholysis reaction to make the desired product. Repolymerization of the glucosides to the less desirable polyglycosides is avoided. In addition undesirable side reactions, which lower yields and give more color bodies, are avoided by the subject method. The composition of the resulting mixed glycosides is surprisingly uniform and consistent in properties. By selectively separating and recovering at least one glucoside from the glycoside mixture and repeatedly or continuously recycling the mother liquor to the reactor, the reactants can be more effectively utilized to achieve optimum production of the desired end product.

DETAILED DESCRIPTION OF THE INVENTION

This invention relates to a continuous alcoholysis process for making mixed aldosides from carbohydrates and selectively removing at least one aldoside therefrom. In the present process an aldoside mixture is produced by slurrying a carbohydrate in an alcohol containing media and passing it through a confined zone under fluid pressure at an elevated temperature in the presence of an acid catalyst. Mixed hydrocarbyl aldosides containing a high proportion of monoaldosides (i.e. alpha- and beta-) may be prepared from monosaccharides and/or polysaccharides by this process. The resultant aldoside mixture may then be partitioned into a mother liquor portion and glucoside portion by selectively partitioning at least one hydrocarbyl aldoside from the crude aldoside mixture. The partitioned aldoside is recovered therefrom and the mother liquor is recycled to the converter.

In the present process, the feed slurry is continuously provided to a tubular reaction zone under a positive fluid pressure. Although starch is the preferred carbohydrate reactant the feed slurry reactants may broadly encompass monohydric alcohols and carbohydrates. Monosaccharides (e.g. dextrose, etc.), polysaccharide materials (e.g. hemi-cellulose, inulin, dextran, xylan and the like) and/or mixtures (e.g. corn syrup solids) thereof may be "alcoholized" to aldosides in the presence of a catalyst to form the corresponding aldosides under the appropriate temperatures and pressures.

Illustrative monohydric alcohols include the aliphatic alcohols (saturated or unsaturated) such as the $C_1$-$C_{18}$ alkanols and $C_3$-$C_{18}$ alkenols. Exemplary aliphatic monohydric alcohols include methanol, ethanol, propanol, allyl alcohol, butanol, alcohols having five to eighteen carbon atoms, their isomers, derivatives and mixtures thereof. The process is particularly well adapted for the alcoholysis of starch with the $C_1$-$C_4$ monohydric alcohols and especially methanol. The monohydric alcohol serves as a reactant and as a liquid dispersant throughout the entire process. Accordingly, the alcohol functions as a dispersant for the chemical reactants and as a solvent for the reaction products from which the desired end product may be effectively crystallized. The amount of monohydric alcohol used in the process should be sufficient to maintain the reactor feed slurry and reaction product in a fluidized state. A molar excess of alcohol is typically needed for this purpose. When starch is utilized, the monohydric alcohol to starch molar ratio will most generally range from about 15:1 to about 6.5:1. In the alcoholysis of starch with methanol, the starting feed slurry will typically contain from about 30% to about 50% by weight starch and from 50% to about 70% by weight methanol.

The alcoholysis of the carbohydrate is conducted in the presence of sufficient acid catalyst to catalyze the reactants to an alkyl aldoside mixture. Although the catalyst concentration may vary considerably, a catalyst concentration from about 0.001 to about 0.1 mole catalyst per mole of starch may typically be used. Illustrative acid catalysts therefore include hydrochloric acid, sulfuric acid, phosphoric acid, ortho-, meta-, and para-toluene-sulfonic-acid, benzene-sulfonic acid, various substituted benzene-sulfonic acids, such as ortho-, meta-, and para-bromo-benzene-sulfonic acids, ethanesulfonic acid and the like, as well as combinations thereof. When starch is used as a starting reactant, the preferred catalyst concentration is advantageously at least 0.004 mole catalyst per starch mole and preferably in an amount ranging from about 0.005 to about 0.01 mole of catalyst for each mole of starch.

As previously mentioned, the chemical reaction is appropriately conducted within a tubular reaction zone suitably equipped with heating means sufficient to convert the reactants into the desired aldoside mixture. Apparatus of the type disclosed in U.S. Pat. Nos. 2,735,792 and 3,617,383 may be appropriately adapted to the present process. The continuous coil of the reactor may be of any convenient length (e.g. 50–5000 ft.) and inner diameter (e.g. about 0.18 inch to about 6 inches). The chemical reaction should be conducted within the reactor for a period of time and at a temperature sufficient to convert the reactants into the desired aldoside mixture. Although these temperature-time conditions can vary considerably, the temperature will generally range between about 100° C. to about 400° C. for a period of time ranging from about 2 to about 150 minutes. Prolonged exposure of the reactants to elevated temperatures which result in charring or excessive formation of non-glucoside by-products should be avoided. Conversely, low temperatures can lead to plugging or fouling of the reactor and incomplete glycoside conversion. If the reactants are comprised of starch and methanol, the reactants will advantageously have a residence within the reactor of less than about 30 minutes (e.g. 2–30) and preferably less than about 20 minutes (e.g. about 5–20 minutes). The reaction will usually be conducted at a temperature greater than 160° C. (e.g. about 160° C. to about 180° C.) and preferably at a temperature of at least 165° C. The feed slurry and reaction products are forced through the reaction zone under a positive fluid pressure. Means for providing the feed slurry to the reactor under positive pressure (e.g. pumps, etc.) at a controlled pressure and rate (e.g. valves, pressure regulators, etc.) may be suitably used for this purpose. Means to automatically measure and meter the flow of reactants through the reactor and to replenish the reactants in the correct proportions in the feed pressure vessel may also be appropriately adapted to the process. A second feed pressure vessel with valves may be provided in a parallel line so that the reactants may be alternately fed to the continuous coil reactor from either pressure feed vessel as desired.

Under the proper processing conditions (e.g. temperature, pressure, catalyst, reaction media and time, etc.), the composition of the reaction mixture will remain relatively constant. The consistency and reproducibility of the equilibrated glycoside mixture via the present process provides a means whereby the reaction by-products may be effectively recycled and used to optimize the production of the desired glycoside reaction product.

The chemical reactivity and type of reactants used to prepare the aldosides will affect the relative proportion of mono-, di-, tri- and higher aldosides, including their isomeric forms, in the aldoside mixture. As further illustrated by the examples, modification of the reaction conditions may also alter these proportions. Under any given set of processing conditions, a relatively constant proportion of aldoside components will be produced for any given reactant system. Accordingly, any given reaction system can be satisfactorily and uniformly reproduced by controlling the processing conditions under which the aldoside mixtures have been prepared.

When starch and methanol are subjected to the alcoholysis process of this invention, the equilibrated glycoside mixture will generally yield methyl-D-glucopyranosides (alpha- and beta-forms) as the major reaction products (solid weight basis). The alpha isomer is typically the most predominant reaction product (i.e. its weight exceeds all other glycosides) of the mixture. For most operations, the methyl-D-glucopyranosides content (alpha- and beta-forms) will typically range from about 65% to about 90% by weight of the total non-volatile solids of the glycoside mixture. The proportion of alpha-isomer can be altered by changing the reaction conditions. The alpha isomer content will generally range from greater than 25% to less than about 75% by weight of the total non-volatile mixture solids. Because of recovery considerations, it is generally desirable to maximize the alpha-glucopyranoside isomer yield. Methyl-alpha-D-glucopyranoside recovery is promoted by operating under reaction conditions which yield a glycoside mixture containing at least 40% by weight methyl-alpha-D-glucopyranoside (solids basis). It is expedient and advantageous to normally produce a glycoside mixture which contains at least 45% by weight alpha isomer with an amount ranging from about 45% to 60% being the most typical operational range.

When the methyl-alpha-D-glucopyanoside isomer is the predominant reaction product, the methyl-beta-D-glucopyranoside is typically the second most prevalent product of the reaction mixture. It will usually range from about 40% to about 60% of the alpha isomer weight with an amount between about 20% to about 35% by weight of the total glycoside mixture solids being most typical thereof. Under such conditions, the remaining glucosidic isomers (i.e. methyl-alpha-D-glucofuranoside and methyl-beta-D-glucofuranoside) will normally constitute a considerably smaller proportion (less than 20% and preferably less than 15%) of the total glycoside mixture solids weight. Preferably the total furanoside (alpha- and beta-) content of the glycoside mixture will be less than 10% by weight with an amount ranging from about 5% to about 8% being most typical thereof.

Other than the glucopyranosides, the methyl-D-maltosides (alpha- and beta-forms) will normally comprise the major constituent (weight basis) of the remaining solids in the glycoside mixture. These diglycosides will generally constitute less than 20% by weight of the total glycoside mixture solids with an amount ranging from about 8% to about 15% by weight being most typical thereof. When the process conditions are adjusted to optimize alpha-glucopyranoside production, the triglycosides (e.g. methyl-alpha-D-maltotrioside and methyl-beta-D-maltotrioside) will usually comprise a smaller proportion (e.g. less than 5%) of the glycoside mixture with levels ranging from about 1% to 4% being most common. Under such process conditions, the oligosides (i.e. $>$D.P.$_3$ glycosides) will constitute but a very small amount of the glycoside mixture weight (e.g. less than 1% and most typically less than 0.5%). As evident from the relatively small proportion of triand oligosides, the process conditions herein effectively produce glucosides and inhibit their repolymerization into polyglucosides.

Under the appropriate processing conditions, the methyl-alpha-D-glucopyranoside content of the glycoside mixture (on a dry weight ratio basis) may be designed to exceed the methyl-beta-D-glucopyranoside by at least a 3:2 weight ratio (e.g. about 1.5–3 times greater), the methyl-alpha-D-maltoside and methyl-beta-D-maltoside content by at least 3:1 (e.g. between 3:1 and about 6:1), the methyl-alpha-D-maltotrioside and methyl-beta-D-maltotrioside content by at least 10:1 (e.g. between 11:1 and about 50:1), the methyl-alpha-D-glucofuranoside and methyl-beta-D-glucofuranoside by at least 6:1 (e.g. 6:1 to about 10:1) and the higher methyl-alpha- and beta-oligosides (i.e. $>$D.P.$_3$) by at least 35:1 (e.g. between 38:1 to about 740:1). Other non-glycoside reaction by-products such as dextrose will typically comprise less than about 5% of the total reaction product dry solids weight.

As further illustrated by our copending application, glycoside mixtures comprising (on a weight percent basis) from about 45.67–51.54% methyl-alpha-D-glucopyranoside; 25.88–27.96% methyl-beta-D-glucopyranoside; 8.67–14.73% methyl-alpha-D-maltoside and methyl-beta-D-maltoside; 1.04–3.92% methyl-alpha-D-maltotrioside and methyl-beta-D-maltotrioside; 0.07–1.19% higher methyl-alpha- and beta-oligosides; 5.26–7.54% methyl-alpha-D-glucofuranoside and methyl-beta-D-glucofuranoside; and 1.02–3.34% dextrose are easily obtainable by the present process.

The present invention broadly applies to the alcoholysis of carbohydrates with monohydric alcohols to produce an aldoside mixture and partitioning at least one aldoside therefrom.

Crude glycoside mixtures produced by the present method provide a particularly suitable substrate for selectively removing at least one hydrocarbyl glucoside and the recycling of the balance of the glycoside mixture to the tubular reactor as feed stock. A variety of conventional techniques for partitioning and recovering hydrocarbyl glucosides from glycoside mixtures may be used (e.g. chromatographic, membrane separation, diffusion, crystallization, etc.). Crystallization is the preferred method of product separation and recovery.

The most suitable conditions for crystallizing and recovering at least one aldoside from the resultant aldoside mixture will depend upon the crystalling characteristics (e.g. saturation, concentration, crystallizing temperature, etc.) for the particular aldoside crystallite to be recovered from the aldoside mixture. The most appropriate crystalling conditions may be ascertained by means of conventional supersaturation and crystallization temperature curves. Such curves may be effectively utilized to optimize crystal yields for batch or continuous crystalling (e.g. progressively concentrating the mixture and gradationally cooling to maintain optimum critical saturation concentration for continuous crystal recovery) operations.

The process is particularly adapted for the crystallization and recovery of methyl-alpha-D-glucopyranoside because of its lower solubility in alcohols. This will provide a mother liquor rich in the remaining components of the glycoside mixture. The return of the mother liquor to the methanolysis reaction, in which more starch and methanol are added, results in substantial quantitative conversion of the starch to methyl-alpha-D-glucopyranoside.

A particularly unique attribute of the present invention is the ability to produce an equilibrated reaction product containing a high proportion of methyl-alpha-D-glucopyranoside which can be easily removed therefrom by crystallization. This will provide a mother liquor which contains an excess of the reaction products other than methyl-alpha-D-glucopyranoside. When this mother liquor is recycled to the reactor, the reaction media contains its complement of reaction products other than methyl-alpha-D-glucopyranoside. As a result of this deficiency, the chemical reaction will be driven almost entirely towards the production of methyl-alpha-D-glucopyranoside since essentially all of the remaining by-products for the equilibrated chemical reaction are already present in the recycled mother liquor.

Although the methyl-alpha-D-glucopyranoside concentration obtained from the reaction is sufficient to permit its direct crystallization from the glycoside mixture upon cooling, more effective methyl-alpha-D-glucopyranoside crystallization and recovery may be accomplished by concentrating the glycoside mixture. This will increase the methyl-alpha-D-glucopyranoside supersaturation temperature and reduce the overall cooling requirements for satisfactory crystallization.

In the present process, it is advantageous to immediately flash-cool, without solidifying, the glycoside mixture as it issues from the reactor. Flash-cooling facilitates hydrocarbyl-alpha-D-glucoside crystallization by increasing the glycoside solids concentration. In addition to concentrating the glycoside mixture, flash-cooling will terminate the chemical reaction and alleviate undesirable by-product production repolymerization. If desired, the volatiles of the flash-cooling (methanol and water) may be recovered by conventional means and recycled into the process.

The amount of methyl-alpha-D-glucopyranoside produced with each pass through the converter will be inversely proportional to its level in the mother liquor. It is therefore advantageous to remove as much methyl-alpha-D-glucopyranoside as commercially feasible from the glycoside mixture before recycling the mother stream to the reactor. Overall methyl-alpha-D-glucopyranoside production will be impaired if less than one-fourth of the total methyl-alpha-D-glucopyranoside within the glycoside mixture is removed before the mother liquor is recycled to the reactor. For most operations, it is advantageous to leave a minor portion (preferably about 25% to about 40%) of the total methyl-alpha-D-glucopyranoside in the mother liquor and recycle it to the reactor.

In the crystallization of methyl-alpha-D-glucopyranoside from the glycoside mixture, the mixture is cooled sufficiently to permit the glucoside to crystallize therefrom. The crystalling temperature will depend upon the methyl-alpha-D-glucopyranoside concentration. For commercial purposes, the dry solids content of the glycoside mixture will typically be concentrated from about 40% to about 80% and preferably from about 50% to about 75%. At this concentration, methyl-alpha-D-glucopyranoside may be typically crystallized therefrom at a crystallization temperature ranging from about 5° C. to about 50° C. and preferably within a temperature ranging from about 15° C. to about 35° C.

If desired, the crystalling temperature may be incrementally decreased to optimize crystallization of the methyl-alpha-D-glucopyranoside from the glycoside mixture. Likewise, the solids concentration of the glycoside mixture may be periodically adjusted to take into account the glucoside crystallized therefrom so as to permit the recovery of additional glucoside therefrom. Alternatively the glycoside mixture may be subjected to a series of crystallization steps with the mixture being concentrated between each successive batch. Similarly, the glucoside may be continuously crystallized and recovered from a glycoside mixture by progressively decreasing the crystallization temperature with or without simultaneous or intermittent concentration of the glycoside mixture. Conventional seeding techniques may also be used, if desired, to expedite crystallite formation in the glycoside mixture. If more than one aldoside is to be recovered from the mixture, the least soluble aldoside component may be exhaustively crystallized followed by the crystallization therefrom of the next least soluble aldoside component (e.g. see U.S. Pat. No. 3,565,885).

The hydrocarbyl glucoside crystallites may be recoverd from the glycoside mixture by conventional recovery techniques (e.g. via filtration, centrifugation, etc). Under proper washing and extraction techniques, the purity of the hydrocarbyl glucoside crystals will be significantly improved. Surface and non-occluded contaminants may be conveniently removed from the hydrocarbyl crystals by conventional cold washing techniques. Washing the crystals with monohydric alcohol at a cool temperature (e.g. 15° C. to 25° C.) is generally sufficient to remove these contaminants therefrom and to provide the desired purified product. For example, washed crystalline methyl-alpha-D-glucopyranoside containing less than 1% methyl-beta-D-glucopyranoside, less than 2% and preferably less than 1.5% maltosides, less than 0.5% oligosides, less than 1% dextrose (preferably less than 0.5%), essentially free from furanosides and less than about 0.5% of other impurities may be prepared.

To maintain an adequate recoverable yield of aldoside in a continuous operation, it is generally necessary to fortify the mother liquor with reactants and catalyst. After the initial run, the mother liquor will typically contain its full complement of reaction by-products (i.e. those not recovered from the mother liquor) except for those minor impurities removed from the aldoside mixture during the partitioning step. Satisfactory conversion and recovery of the desired aldoside from the aldoside mixture will generally necessitate additional carbohydrate to be added to the recycled stream. The overall carbohydrate requirement for recycled feed stream is significantly reduced because the recycled mother liquor will typically contain substantially its full complement of aldoside by-products. Accordingly, the use of the recycled mother liquor as a feed slurry component provides reaction medium whereby substantially all of the carbohydrate may be directly converted into the desired end product. When methyl-alpha-D-glucopyranoside is the desired product, the amount of starch typically added to the feed slurry should advantageously be sufficient to maintain a yield of at least 40% and preferably at least 45% by weight methyl-alpha-D-glucopyranoside. A portion of these yield requirements will be normally fulfilled by the unrecovered residual methyl-alpha-D-glucopyranoside which is recycled with the mother liquor to the conversion zone. The molar requirements for satisfactory conversion of other carbohydrates may likewise be computed on the basis of their reaction equations.

In the conversion process, the mother liquor will normally lack a sufficient amount of monohydric alcohol to maintain a satisfactory end product yield. This deficiency will arise because of direct conversion of the alcohol reactant into the recovered product and the evaporative losses which arise from concentrating the aldoside mixture to effectively crystallize and recover the methyl-alpha-D-glucopyranoside therefrom. The amount of alcohol added to the recycled feed slurry should be sufficient to maintain satisfactory yields of the desired end product as well as to provide a feed slurry having the necessary fluidity prerequisite to be processed in accordance with the processing conditions of this invention.

Under normal operations, a small amount of catalyst will be physically lost by the processing conditions. Small amounts of catalyst, as needed, may be accordingly added to the recycled feed slurry to insure adequate conversion of the reactants into the desired conversion product.

As further illustrated by the examples, crystalline methylalpha glucoside of a purity of at least 94% and most preferably at least 96% may be easily prepared by the present process. The purity of the methyl-alpha-D-glucopyranoside crystals is not adversely affected by continuous recycling and reuse of the mother liquor.

The following examples are illustrative of the invention.

EXAMPLE 1

In this example, a starch slurry was continuously converted in a continuous coil reactor (360 feet long and 0.305 inch internal diameter) submerged in a hot hydrogenated vegetable oil bath. The continuous reactor was continuously fed by means of a nitrogen pressurized Parr vessel. The effluent reaction product issuing from the reactor was flash-cooled (under atmospheric pressure and ambient temperature) and collected in two liter graduated cylinders.

Starch containing about 5% moisture was slurried in methanol at 43% solids. About 0.005 moles of p-toluene-sulfonic acid per mole AGU (anhydroglucose unit) was added. The continuous reactor was adjusted to maintain the starch/acid alcohol slurry mixture at a temperature of about 165° C. through. The pressure control means was adjusted to obtain about ten minutes retention time in the continuous coil reactor.

There was obtained a crude methyl glycoside product (after flashing to atmospheric pressure) containing 62% solids solution in methanol. The solids analyzed as follows:

| | |
|---|---|
| 48.0% | methyl-alpha-D-glucopyranoside |
| 25.0% | methyl-beta-D-glucopyranoside |
| 6.0% | methyl-alpha-D-glucofuranoside and methyl-beta-D-glucofuranoside |
| 13.5% | methyl-alpha-D-maltoside and methyl-beta-D-maltoside |
| 3.0% | methyl-alpha-D-maltotrioside and methyl-beta-D-maltotrioside |
| 0.3% | higher methyl-alpha- and beta-oligosides |
| 2.0% | dextrose |
| 1.5% | unidentified component (possibly a 5-carbon reducing sugar) |
| 0.7% | residual catalyst and/or moisture |
| 100.0% | |

EXAMPLE 2

The following results were obtained by decreasing the methanol/starch molar ratio. The methanol/starch ratio was decreased in seven steps from 15:1 to 6.8:1, while maintaining all other variables constant. All runs were at 172° C., 16 minutes retention time, using 0.01 mole of para-toluene sulfonic acid catalyst per mole of anhydroglucose unit (AGU) based on starch adjusted to 5% moisture. As set forth below, it can be seen that this change reduced the percentage of methyl-alpha and beta-glucosides in the crude product while the levels of dextrose and polyglycosides increased. The results of this study are tabulated in Table I.

TABLE I

| EFFECT OF DECREASING METHANOL:STARCH RATIO OF PRODUCT COMPOSITION | | | | | | | |
|---|---|---|---|---|---|---|---|
| Sample | A | B | C | D | E | F | G |
| Moles Methanol/Mole AGU | 15.0 | 12.5 | 10.7 | 9.4 | 8.3 | 7.5 | 6.8 |
| Product Composition: | | | | | | | |
| methyl-alpha-D-glucopyranoside, % | 51.54 | 51.46 | 50.27 | 50.01 | 48.72 | 47.38 | 45.67 |
| methyl-beta-D-glucopyranoside, % | 27.96 | 27.74 | 27.82 | 27.11 | 26.37 | 26.17 | 25.88 |
| methyl-alpha-D-maltoside and methyl-beta-D-maltoside, % | 8.67 | 9.45 | 10.54 | 11.24 | 12.53 | 13.37 | 14.17 |
| methyl-alpha-D-maltotrioside and | | | | | | | |

TABLE I-continued
EFFECT OF DECREASING METHANOL:STARCH RATIO OF PRODUCT COMPOSITION

| Sample | A | B | C | D | E | F | G |
|---|---|---|---|---|---|---|---|
| methyl-beta-D-maltotrioside, % | 1.04 | 1.01 | 1.36 | 1.62 | 2.26 | 2.51 | 3.10 |
| higher methyl-alpha- and beta-oligosides, % | 0.08 | 0.05 | 0.06 | 0.09 | 0.10 | 0.13 | 0.18 |
| methyl-alpha-D-glucofuranoside and methyl-beta-D-glucofuranoside, % | 7.54 | 7.28 | 6.93 | 6.66 | 6.57 | 6.73 | 6.78 |
| Dextrose, % | 1.02 | 1.16 | 1.46 | 1.65 | 1.77 | 2.01 | 2.33 |
| Other and unidentified, % | 2.15 | 1.84 | 1.66 | 1.62 | 1.67 | 1.70 | 1.88 |

In the above Table I, it can be seen the Sample A product yielded 79.5% methyl-alpha-D-glucopyranoside and methyl-beta-D-glucopyranoside, and only 10.81% of polyglycosides and dextrose. Sample D produced 77.12% methyl-alpha-D-glucopyranoside and methyl-beta-D-glucopyranoside, while Sample G produced only 71.55% of the glucosides. At the same time, the percentages of polyglycosides and dextrose increased as the methanol:starch ratio decreased. The cost of removal of excess methanol must be balanced against the slightly increased yield of glucosides.

EXAMPLE 3

Tests were made to determine the effect of reducing the amount of catalyst used. Para-toluene sulfonic acid was reduced from 0.01 to 0.005 mole/mole AGU (anhydroglucose unit) in a series of tests. There was no observable change in the chemical composition of the product. However, at 0.0034 mole catalyst/mole AGU, the reactor plugged. Product color at the 0.005 mole catalyst level was significantly lighter than at higher levels. All runs were conducted at 6.8:1 moles methanol:mole AGU, 172° C., a 15–16 minutes retention time and PFP starch at 5.0% moisture. The results for four samples having various levels of para-toluene sulfonic acid catalyst are set forth below:

TABLE II
Effect of Catalyst Level on Product Composition

| Sample | H* | I | J | K |
|---|---|---|---|---|
| Moles Catalyst/Mole AGU | 0.010 | 0.0066 | 0.0050 | 0.0034 |
| Product Composition: | | | | |
| methyl-alpha-D-glucopyranoside, % | 45.67 | 46.31 | 46.64 | |
| methyl-beta-D-glucopyranoside, % | 25.88 | 25.62 | 25.75 | |
| methyl-alpha-D-maltoside and methyl-beta-D-maltoside, % | 14.17 | 14.40 | 14.31 | Not |
| methyl-alpha-D-maltotrioside and methyl-beta-D-maltotrioside, % | 3.10 | 3.18 | 2.93 | Analyzed |
| higher methyl-alpha- and beta-oligosides, % | 0.18 | 0.16 | 0.12 | |
| methyl-alpha-D-glucofuranoside and methyl-beta-D-glucofuranoside, % | 6.78 | 6.96 | 6.87 | |
| Dextrose, % | 2.33 | 1.70 | 1.67 | |
| Other and unidentified, % | 1.88 | 1.66 | 1.70 | |
| Color | Dk.Brown | Brown | Cream | |

*Same as Sample G, Table I.

Sample K was not analyzed because it plugged the reactor. It appears that a different reactor design may be required for lower catalyst levels. The preferred amount of catalyst using the present reactor is about 0.0050 mole/catalyst/mole AGU, although 0.004 mole catalyst/mole AGU was used in one comparison in Example 4, below.

EXAMPLE 4

Tests were also done to determine the effect of temperature on the resulting being composition. All runs were conducted at 6.8:1 moles methanol:mole AGU, 0.005 mole p-TSA/Mole AGU, 16 minutes retention time on PFP starch at 5.0% moisture. Temperature of the reaction mixture was changed in four steps from 178° C. to 161° C. with the results reported in table III.

TABLE III
Effect of Reaction Temperature on Product Composition

| Sample | L | M | N | O |
|---|---|---|---|---|
| Product Composition: | | | | |
| methyl-alpha-D-glucopyranoside, % | 45.79 | 45.89 | 47.29 | 46.61 |
| methyl-beta-D-glucopyranoside, % | 25.96 | 25.80 | 26.21 | 25.92 |
| methyl-alpha-D-maltoside and methyl-beta-D-maltoside, % | 13.70 | 14.53 | 13.87 | 14.14 |
| methyl-alpha-D-maltotrioside and methyl-beta-D-maltotrioside, % | 2.97 | 3.08 | 2.89 | 3.49 |
| higher methyl-alpha- and beta-oligosides, % | 0.23 | 0.29 | 0.28 | 1.19 |
| methyl-alpha-D-glucofuranoside and methyl-beta-D-glucofuranoside, % | 6.97 | 6.42 | 6.15 | 5.78 |
| Dextrose, % | 2.08 | 1.91 | 1.66 | 1.51 |
| Other and unidentified, % | 2.29 | 2.08 | 1.64 | 1.35 |
| Reaction Temp., °C. | 178 | 172 | 166 | 161 |
| Color | Brown | Dark Tan | Tan | Cream |

In another experiment, the reaction temperature was increased to 181° C. while decreasing the catalyst 0.004 mole/mole AGU. Product composition showed only minor changes in almost all components when compared to a run at 172° C. where catalyst level was 0.005 mole/mole AGU. Color was significantly poorer, however.

As can be seen above in Table III, product color improves from brown to cream. The chemical composition changed very little with the only significant increase occurring in the higher glycosides at the lowest temperature.

EXAMPLE 5

The combined effect of reducing the reaction temperature to 152° C. while increasing the retention time to 26 minutes was compared to a run at 172° C. and 16 minutes retention time. The results are reported in Table IV.

TABLE IV
Effect of Low Temperature and Increased Retention Time on Composition

| Sample | P* | Q |
|---|---|---|
| Product Composition: | | |
| methyl-alpha-D-glucopyranoside, % | 46.31 | 47.65 |
| methyl-beta-D-glucopyranoside, % | 25.62 | 26.20 |
| methyl-alpha-D-maltoside and | | |
| methyl-beta-D-maltoside, % | 14.40 | 14.47 |
| methyl-alpha-D-maltotrioside and | | |
| methyl-beta-D-maltotrioside, % | 3.18 | 3.04 |
| higher methyl-alpha- and beta-oligosides, % | 0.16 | 0.42 |
| methyl-alpha-D-glucofuranoside and | | |
| methyl-beta-D-glucofuranoside, % | 6.96 | 5.01 |
| Dextrose, % | 1.70 | 1.79 |
| Other and unidentified, % | 1.66 | 1.42 |
| Reaction Temperature, °C. | 172 | 152 |
| Retention time, min. | 16 | 26 |

*Same as Sample I, Table II.
(Both runs at 6.8:1 mole methanol/mole AGU, 5% moisture on feed starch, 0.0066 mole p-TSA/Mole/AGU.)

It can be see in Table IV that the combination of lower reaction temperature and longer retention time did not avoid the trend on increase in higher oligosides and dextrose observed above in Table III. The results reported in Table IV indicate that the higher temperature of Sample P is preferred to avoid an increase of higher oligosides and dextrose, even though the amount of methyl-glucopyranoside did decrease in this comparison.

EXAMPLE 6

The effect of feed starch moisture on product quality was also checked by conducting four runs at feed starch moisture levels ranging from 2% to 11%. The results are reported below:

TABLE V
Effect of Feed Starch Moisture on Product Composition

| Product Composition: | R | S | T | U |
|---|---|---|---|---|
| methyl-alpha-D-glucopyranoside, % | 48.17 | 45.05 | 45.78 | 48.59 |
| methyl-beta-D-glucopyranoside, % | 26.78 | 28.46 | 27.86 | 26.33 |
| methyl-alpha-D-maltoside and | | | | |
| methyl-beta-D-maltoside, % | 12.67 | 13.16 | 12.76 | 11.88 |
| methyl-alpha-D-maltotrioside and | | | | |
| methyl-beta-D-maltotrioside, % | 2.49 | 2.40 | 2.23 | 2.09 |
| higher methyl-alpha- and beta-oligosides, % | 0.07 | 0.09 | 0.07 | 0.15 |
| methyl-alpha-D-glucofuranoside and | | | | |
| methyl-beta-D-glucofuranoside, % | — | 7.32 | 7.00 | 6.48 |
| Dextrose, % | 1.07 | 1.68 | 2.22 | 2.74 |
| Other and unidentified, % | — | 1.84 | 2.09 | 1.73 |
| Feed starch moisture, % | 2.00 | 5.00 | 8.00 | 11.00 |

(All runs at 8.3:1 moles methanol:mole AGU, 0.005 mole p-TSA/mole AGU, 14.5 minutes retention time, 172° C.).

It can be seen from the above results in Table V that the percentage of dextrose produced increases as moisture increases. Quite surprisingly the product also becomes unexpectedly lighter. This improvement in color is opposite to the expected trend. It would be expected that higher dextrose levels would cause darker color. Starch is usually available at about 10–13% moisture, and the above results show that it is not necessary to predry the starch prior to use in the subject process.

EXAMPLE 7

Tests were carried out to determine the effect of retention times on product composition. Retention times of 16.5, 10.7 and 8.0 minutes in the reactor were compared with the results reported below:

TABLE VI

| Product Composition: | V | W | X |
|---|---|---|---|
| methyl-alpha-D-glucopyranoside, % | 44.88 | 45.66 | 43.21 |
| methyl-beta-D-glucopyranoside, % | 27.68 | 27.58 | 27.54 |
| methyl-alpha-D-maltoside and | | | |
| methyl-beta-D-maltoside, % | 14.44 | 14.04 | 14.73 |
| methyl-alpha-D-maltotrioside and | | | |
| methyl-beta-D-maltotrioside, % | 2.95 | 2.84 | 3.92 |
| higher methyl-alpha- and beta-oligosides, % | 0.25 | 0.25 | 0.85 |
| methyl-alpha-D-glucofuranoside and | | | |
| methyl-beta-D-glucofuranoside, % | 5.26 | 4.79 | 6.03 |
| Dextrose, % | 2.95 | 3.34 | 2.12 |
| Other and unidentified, % | 1.60 | 1.59 | 1.52 |
| Retention time, min., | 16.50 | 10.70 | 8.00 |

(All runs at 6.8:1 moles methanol:mole AGU, 0.005 mole p-TSA/mole AGU, 167° C., PFP starch at 5.0% moisture.)

All of the above runs were performed at 167° C. It can be seen from Table VI that increasing the retention time from 8 to 16.5 minutes favors increased methyl-alpha-D-glucopyranoside yields, and a decrease in the levels of polyglycosides.

EXAMPLE 8

In this example, a methyl glycoside mixture was continuously prepared according to Example 1 except the pressurized vessel was replaced with a high pressure pump to transfer and force the feed slurry through the reactor. After each cycle through the reactor, a portion of the methyl-alpha-D-glucopyranoside was recovered from the glycoside mixture. The balance of the unrecovered methyl-alpha-D-glucopyranoside was then recycled, as part of the mother liquor, to the feed slurry. Supplemental amounts of starch, methanol and catalyst (as needed) were added to the mother liquor to maintain a satisfactory yield of methyl-alpha-D-glucopyranoside. The parts by weight material used for the initial startup reaction, the supplemental amounts of reactants and catalyst added to the mother liquid for each recycle, the percentage of non-volatiles produced in each recycled feed slurry and the yield of recovered crystalline methyl-alpha-D-glucopyranoside (parts by weight and its percentage of the total weight of non-volatile reaction product solids) for each successive pass through the reactor are tabulated in Table VII.

TABLE VII

| | INITIAL RUN | RECYCLE 1 | RECYCLE 2 | RECYCLE 3 | RECYCLE 4 | RECYCLE 5 |
|---|---|---|---|---|---|---|
| Methanol | 16,000 | 5,140 | 4,311 | 5,070 | 3,287 | 5,605 |
| Starch (d.s.) | 8,100 | 1,873 | 1,419 | 1,670 | 1,536 | 1,766 |
| H₂O (from starch) | 426 | 99 | 75 | 88 | 81 | 93 |
| Recycle of mother liquor (as is) | 0 | 10,121 | 12,593 | 12,604 | 13,127 | 12,547 |
| p-TSA | 57 | 13.2 | 10.3 | 0 | 0 | 0 |

TABLE VII-continued

|  | INITIAL RUN | RECYCLE 1 | RECYCLE 2 | RECYCLE 3 | RECYCLE 4 | RECYCLE 5 |
|---|---|---|---|---|---|---|
| TOTAL WEIGHT, g | 24,583 | 17,246 | 18,408 | 19,432 | 18,031 | 20,011 |
| % solids | 32.9 | 32.1 | 32.8 | 29.9 | 35.9 | 32.1 |
| Crystalline Harvest p.b.w. | 2,244 | 1,699 | 1,670 | 1,536 | 1,766 | 1,678 |
| Harvest as % of Total solids, d.s. | 33.7 | 27.1 | 26.5 | 26.3 | 27.2 | 25.9 |

On a non-volatile weight basis, the composition of the methyl glycoside obtained from the initial run consisted of methyl-alpha-D-glucopyranoside 49.95%, methyl-beta-D-glucopyranoside 27.19%, methyl-alpha and methyl-beta-D-glucofuranoside 5.95%, methyl-alpha- and methyl-beta-D-maltosides 10.70%, methyl-alpha and methyl-beta-D-maltotriosides 1.57%, methyl-alpha and methyl-beta-D-oligosides 0.12%, dextrose 2.72%, unidentified components 1.38% and other components 0.41%. By maintaining relatively constant reaction conditions a comparable equilibrated reaction product was obtained from each of the ensuring recycle reactions.

In the initial and subsequent recycles, the tubular reactor was maintained at 170° C. with the slurry feed rate being adjusted to provide an average reactor residence time of between 12-15 minutes. The effluent issuing from the tubular reactor for each run was instantaneously flashed to atmospheric pressure. The flash-cooling step concentrated the glycoside mixture to approximately 50% by weight non-volatile solids. Crystallization of the methyl-alpha-D-glucopyranoside was accomplished by cooling the mixture to about 15° C. The crystals were then recovered from the glycoside mixture by filtration, washed with methanol (25° C.) and vacuum-oven dried (60° C. −28 inch mercury).

The composition of the crystalline fraction and mother liquor was determined by liquid chromatographic analysis. The resultant composition for each mother liquor following the recovery of crystalline methyl-alpha-D-glucopyranoside is set forth in Table VIII.

TABLE VIII

| COMPOSITION OF THE MOTHER LIQUOR | | | | | | |
|---|---|---|---|---|---|---|
| Recycled Mother Liquor From | Initial Run | 1 | 2 | 3 | 4 | 5 |
| methyl-alpha-D-glucopyranoside | 27.28 | 32.50 | 29.19 | 32.58 | 29.20 | 28.72 |
| methyl-beta-D glucopyranoside | 40.20 | 39.01 | 39.70 | 38.28 | 38.37 | 38.95 |
| methyl-alpha-D-glucofuranoside and methyl-beta-D-glucofuranoside | 8.98 | 9.31 | 8.93 | 10.11 | 11.19 | 11.16 |
| methyl-alpha-D-maltoside and methyl-beta-D-maltoside | 15.04 | 11.94 | 12.45 | 11.96 | 12.21 | 12.09 |
| methyl-alpha-D-maltotrioside and methyl-beta-D-maltotrioside | 2.05 | 1.21 | 1.39 | 1.24 | 1.49 | 1.26 |
| higher methyl-alpha- and beta-oligosides | .13 | .15 | .48 | .44 | .65 | .74 |
| Dextrose | 3.66 | 3.41 | 4.59 | 3.15 | 3.45 | 3.64 |
| Unidentified | 2.08 | 2.42 | 3.22 | 2.24 | 2.96 | 2.97 |
| Other | .58 | .05 | .05 | — | .48 | .47 |
| Yield, % | 33.7 | 27.1 | 26.5 | 26.3 | 27.2 | 25.9 |

(Ratio of recovered crystals to total weight, d.s., available)

Table IX shows that the present invention affords a means for continuously producing a high purity methyl-alpha-D-glucopyranoside crystalline product from a reaction medium comprised of recycled mother liquor rich in reaction by-products, starch and methanol.

TABLE IX

| Recycle Process - Liquid Chromatographic Analysis of Isolated Crystals and Mother Liquor | | | | | | |
|---|---|---|---|---|---|---|
| Crystals From: | Initial Run | 1 | 2 | 3 | 4 | 5 |
| COMPOSITION | | | | | | |
| methyl-alpha-D-glucopyranoside | 94.54 | 96.52 | 97.11 | 98.39 | 95.57 | 98.08 |
| methyl-beta-D-glucopyranoside | 1.61 | >1 | >1 | >1 | >1 | >1 |
| methyl-alpha-D-glucofuranoside and methyl-beta-D-glucofuranoside | — | — | — | — | — | — |
| methyl-alpha-D-maltoside and methyl-beta-D-maltoside | 2.17 | 1.77 | 1.72 | .88 | 1.26 | .88 |
| methyl-alpha-D-maltotrioside and methyl-beta-D-maltotrioside | .61 | .27 | .29 | — | .78 | .31 |
| higher methyl-alpha and beta-oligosides | .10 | .06 | — | — | 2.02 | .25 |
| Dextrose | .87 | 1.09 | .88 | .66 | .37 | .48 |
| Other | .10 | .30 | — | .07 | — | — |

As illustrated above, the present recycle process affords the means of optimizing the effective use of starch and methanol and directly converting these reactants into the desired methyl-alpha-D-glucopyranoside product. The recycle process provides a means for providing a full complement of the reaction by-products (i.e. methyl-beta-D-glucopyranoside, methyl-alpha- and methyl-beta-D-glucofuranoside, methyl-alpha and methyl-beta-D-maltosides, methyl-alpha- and methyl-beta-D-maltotriosides, methyl-alpha- and methyl-beta-D-oligosides, dextrose, unidentified components and other compounds) which avoids the subsequent unnecessary production of these by-products in the ensuing runs. This permits the recycled reactants to be converted substantially into the desired end product. Although not shown by this example, the methanol is advantageously recovered and recycled into the process (e.g. crystal wash and/or recycled to the feed slurry). It should also be noted that the recycled mother liquor did not adversely affect either the yield or the purity of the recovered crystalline product. Similarly, the mother liquor of recycle 5 and subsequent mother liquors (which could have been obtained by further continuous operation) could have been effectively used to produce further amounts of methyl-alpha-D-glucopyranoside.

What is claimed is:

1. A method for directly converting monohydric alcohols and carbohydrates into aldoside mixtures and recovering therefrom at least one hydrocarbyl aldoside, said process comprising the steps of:

(a) providing to a tubular reaction zone under a positive fluid pressure, a fluid slurry comprised of mother liquor, carbohydrate, monohydric alcohol and catalyst in an amount sufficient to permit chemical conversion of the fluid slurry into a fluid hydrocarbyl aldoside mixture;

(b) heating said feed slurry within said continuous tubular reaction zone to an elevated temperature for a period of time sufficient to convert said fluid slurry into a fluid hydrocarbyl aldoside mixture while continuously providing additional feed slurry to said tubular reaction zone under a positive fluid pressure to force the converted fluid aldoside mixture through said tubular reaction zone;

(c) partitioning the fluid hydrocarbyl aldoside mixture into a mother liquor and aldoside by selectively removing at least a portion of one hydrocarbyl aldoside from the fluid hydrocarbyl aldoside mixture;

(d) recovering the partitioned aldoside therefrom and recycling the mother liquor to the feed slurry of step (a) above.

2. The method according to claim 1 wherein the monohydric alcohol consists essentially of aliphatic monohydric alcohol and the carbohydrate consists essentially of polysaccharide.

3. The method according to claim 2 wherein the carbohydrate consists essentially of starch and the fluid slurry is converted to a glycoside mixture which contains, on a solids weight basis, hydrocarbyl-alpha- and beta-D-glucopyranosides as the major reaction products.

4. The method according to claim 3 wherein the monohydric alcohol is alkanol containing from 1 to 4 carbon atoms inclusive.

5. The method according to claim 3 wherein the monohydric alcohol consists essentially of methanol and the feed slurry is converted to a glycoside mixture containing at least 40% by weight (solids basis) methyl-alpha-D-glucopyranoside.

6. The method according to claim 5 wherein at last 25% of the total weight of the methyl-alpha-D-glucopyranoside of the glycoside mixture is recovered from the glycoside mixture prior to recycling of the mother liquid to the feed slurry.

7. The method according to claim 6 wherein sufficient starch and monohydric alcohol are provided to the reaction zone to permit the feed slurry to be converted into a glycoside mixture containing, on a solids weight basis, at least 45% by weight methyl-alpha-D-glucopyranoside.

8. The method according to claim 7 wherein the feed slurry is converted to a glycoside mixture containing from about 45% to about 60% methyl-alpha-D-glucopyranoside and at least a major weight portion of the methyl-alpha-D-glucopyranoside is crystallized and recovered from the glycoside mixture prior to recycling of the mother liquor to the reaction zone.

9. The method according to claim 8 wherein the glycoside mixture forced through the tubular reaction zone is immediately passed through a cooling zone of a substantially reduced pressure and temperature to cool the glycoside mixture to a temperature below its boiling point.

10. The method according to claim 7 wherein the glycoside mixture is concentrated to a dry solids content ranging from about 50% to about 75% and the methyl-alpha-D-glucopyranoside is crystallized from the glycoside mixture at a crystallization temperature ranging from about 5° C. to about 50° C.

11. The method according to claim 5 wherein the feed slurry is converted to a glycoside mixture containing on a non-volatile solids weight basis from about 65% to about 95% methyl-alpha-D-glucopyranoside and methyl-beta-D-glucopyranoside.

12. The method according to claim 11 wherein at least 45% by weight of the glycoside solids comprises methyl-alpha-D-glucopyranoside.

13. The method according to claim 12 wherein the glycoside mixture forced through the tubular reaction zone is flash-cooled to a temperature below the boiling point of the glycoside mixture.

14. The method according to claim 12 wherein the glycoside mixture is concentrated to a dry solids content between about 40% to about 80% by weight and at least a major weight portion of the methyl-alpha-D-glucopyranoside is crystallized from the mixture at a crystallization temperature ranging from about 5° C. to about 50° C.

15. The method according to claim 13 wherein from about 45% to about 70% of the total methyl-alpha-D-glucopyranoside in the glycoside mixture is recovered from the glycoside mixture with the remaining portion thereof being recycled to the reaction zone.

16. The method according to claim 15 wherein the mother liquor is fortified with sufficient starch and methanol to permit the conversion of the feed slurry into a glycoside mixture containing, on a solids weight basis, at least 45% by weight methyl-alpha-D-glucopyranoside.

17. The method according to claim 16 wherein the glycoside mixture is concentrated to about 50% to about 75% by weight dry solids and the methyl-alpha-D-glucopyranoside is crystallized from the glycoside mixture at a crystallization temperature ranging from about 15° C. to about 35° C.

* * * * *

UNITED STATES PATENT AND TRADEMARK OFFICE
CERTIFICATE OF CORRECTION

PATENT NO. : 4,329,449

DATED : May 11, 1982

INVENTOR(S) : Claris D. Roth; Kenneth B. Moser; William A. Bomball

It is certified that error appears in the above-identified patent and that said Letters Patent are hereby corrected as shown below:

Column 5, line 2, for "charging" read ---charring---
Column 7, line 20, for "crystalling" read ---crystallizing---
Column 7, line 24, for "crystalling" read ---crystallizing---
Column 7, line 28, for "crystalling" read ---crystallizing---
Column 8, line 27, for "crystalling" read ---crystallizing---
Column 8, line 38, for "crystalling" read ---crystallizing---
Column 10, line 17, for "165°C. through" read ---165°C.---
Column 11, line 18, for "the Sample" read ---that the Sample---
Column 12, line 19, for "resulting being composition" read ---resulting composition---

Column 14, Table VI, line 26, for "  V        W        X
                                    1.60     1.59
                                        1.52"
read:---    V        W        X
           1.60     1.52     1.59 ---
Column 17, claim 6, line 45 for "liquid" read ---liquor---

Signed and Sealed this

Ninth Day of November 1982

[SEAL]

Attest:

GERALD J. MOSSINGHOFF

*Attesting Officer*  *Commissioner of Patents and Trademarks*